(12) United States Patent
Gagnon et al.

(10) Patent No.: US 7,961,927 B2
(45) Date of Patent: Jun. 14, 2011

(54) OPTIMAL CONVERSION OF 3D IMAGE SETS BETWEEN DIFFERENT SPACES

(75) Inventors: Daniel Gagnon, Twinsburg, OH (US); Wenli Wang, Aurora, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1060 days.

(21) Appl. No.: 11/719,418

(22) PCT Filed: Nov. 4, 2005

(86) PCT No.: PCT/IB2005/053630
§ 371 (c)(1),
(2), (4) Date: May 16, 2007

(87) PCT Pub. No.: WO2006/054193
PCT Pub. Date: May 26, 2006

(65) Prior Publication Data
US 2009/0123042 A1 May 14, 2009

Related U.S. Application Data

(60) Provisional application No. 60/629,263, filed on Nov. 19, 2004.

(51) Int. Cl.
*G06K 9/36* (2006.01)
(52) U.S. Cl. .................. 382/131; 382/264; 382/300
(58) Field of Classification Search .............. 382/128, 382/131, 154, 284, 299, 300; 378/4; 600/425
See application file for complete search history.

(56) References Cited

U.S. PATENT DOCUMENTS

| 5,299,253 A * | 3/1994 | Wessels .................. 378/163 |
| 6,599,247 B1 | 7/2003 | Stetten |
| 6,628,983 B1 | 9/2003 | Gagnon |
| 6,775,405 B1 * | 8/2004 | Zhu ........................ 382/154 |
| 7,697,738 B2 * | 4/2010 | Da Silva et al. ......... 382/128 |
| 2002/0191734 A1 | 12/2002 | Kojima et al. |
| 2003/0004405 A1 | 1/2003 | Townsend et al. |
| 2003/0199765 A1 | 10/2003 | Stetten et al. |
| 2003/0233039 A1 * | 12/2003 | Shao et al. ............... 600/407 |

(Continued)

FOREIGN PATENT DOCUMENTS

JP          2002214347 A  *  7/2002

(Continued)

OTHER PUBLICATIONS

English translation of Japanese Patent Publication, JP2002214347A, Aug. 2010.*

(Continued)

*Primary Examiner* — Jon Chang

(57) ABSTRACT

A multi-modality system (10) includes a nuclear imaging system (12) and a computed tomography (CT) scanner (14). The nuclear system (12) includes a PET scanner (28) which acquires electronic data that is reconstructed into a PET blob image by a PET reconstruction processor (50). The CT scanner (14) acquires the scanned data which is reconstructed into a 3D CT voxel image by a CT reconstruction processor (56). An interpolation processor (62) interpolates the PET blob image directly into the CT voxel space. Once the PET and CT images are in the same space, they are combined by a combining means (110). A video processor (66) processes the received composite PET-CT data for a display on a monitor (68).

24 Claims, 5 Drawing Sheets

U.S. PATENT DOCUMENTS

Figure 1:
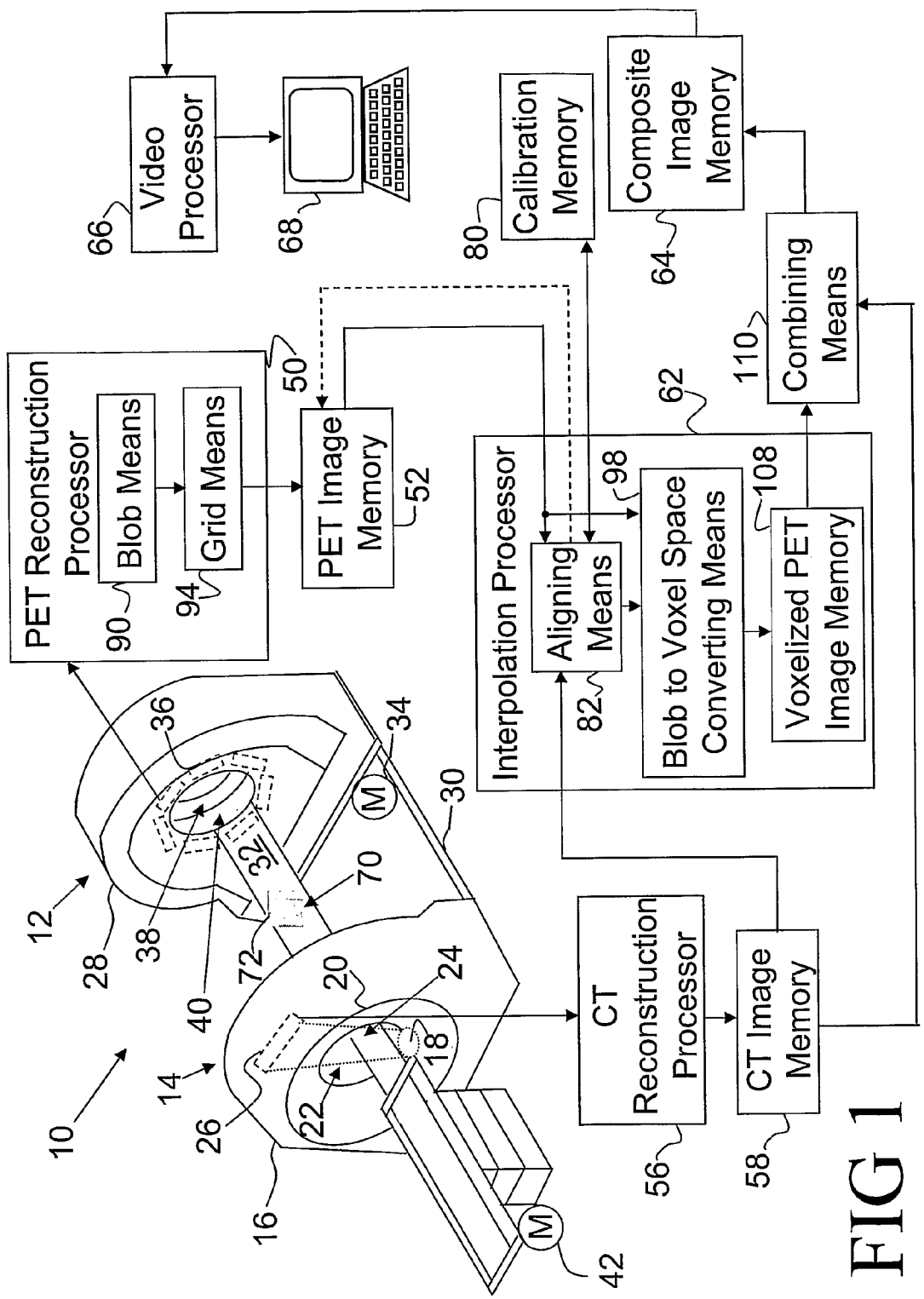

2004/0044282 A1    3/2004   Mixon et al.
2004/0057609 A1    3/2004   Weinberg
2005/0129295 A1*   6/2005   Shanmugam et al. ........ 382/131

FOREIGN PATENT DOCUMENTS

WO          0067202 A1    11/2000
WO          03077202 A1    9/2003

OTHER PUBLICATIONS

Camara et al. "Evaluation of a Thoracic Elastic Registration Method Using Anatomical Constraints in Oncology." Proceedings of the Second Joint EMBS/BMES Conference, Oct. 23, 2002, pp. 1011-1012.*

Tai et al. "Utilization of 3-D Elastic Transformation in the Registration of Chest X-ray CT and Whole Body PET." IEEE Transactions on Nuclear Science, vol. 44, No. 4, Aug. 1997, pp. 1606-1612.*

Luo et al. "Implementation of Mutual Information Based Multi-Modality Medical Image Registration." Proceedings of the 22nd Annual EMBS International Conference, Jul. 23, 2000, pp. 1449-1450.*

Bai, C., et al.; CT-Based Attentuation Correction in PET Image Reconstruction for the Gemini System; 2004; IEEE Nuclear Science Symposium and Medical Imaging Conf.; vol. 5; pp. 3082-3086.

Lewitt, R. M.; Alternatives to voxels for image representation in iterative reconstruction algorithms; 1992; Physics in Medicine & Biology; 37(3)705-716.

Matej, S., et al.; Efficient 3D Grids for Image Reconstruction Using Spherically-Symmetric Volume Elements; 1995; IEEE Nuclear Science Symposium and Medical Imaging Conf.; vol. 3; 1177-1181.

Wang, W., et al.; 3D RBI-EM reconstruction with spherically-symmetric basis function for SPECT rotating slat collimator; 2004; Physics in Medicine and Biology; 49:2273-2292.

Lewitt, R. M.; Multidimensional Digital Image Representations Using Generalized Kaiser-Bessel Window Functions; 1990; J. Opt. Soc. Am.; 7(10).

Jacobs, et al.; Iterative Image Reconstruction from Projections Based on Generalized Kaiser-Bessel Window Functions; 1999; 1st World Congress on Indus. Process Tomography, Buxton, Greater Manchester.

Yendiki, et al.; A Comparison of Rotation-and-Blob-Based System Models for 3-D SPECT with Depth-Dependent Detector Response; U. Michigan, Ann Arbor, MI, US.

Garduno, et al.; Optimization of Basis Functions for Both Reconstruction and Visualization; 2002; Discrete Applied Mathematics.

* cited by examiner

OPTIMAL CONVERSION OF 3D IMAGE SETS BETWEEN DIFFERENT SPACES

CROSS REFERENCE TO RELATED APPLICATIONS

This application claims the benefit of U.S. provisional application Ser. No. 60/629,263 filed Nov. 19, 2004, which is incorporated herein by reference.

The present invention relates to the diagnostic imaging systems and methods. It finds particular application in conjunction with multi-modality systems, such as PET-CT systems. It will be appreciated that the invention is also applicable to the various combinations of SPECT, CT, ultrasound, MRI, fluoroscopy, and the like.

In multi-modality tomographic systems, two or more different sensing modalities are used to locate or measure different constituents in the object space. In the PET-CT system, the PET creates images of high metabolic activity in the body, rather than creating images of surrounding anatomy. CT scans allow doctors to see the internal structures within the human body. Before having a PET-CT scan, the patient receives a dose of a radiopharmaceutical. The pharmaceutical is carried through the blood and concentrates in a particular organ or region and causes radiation to be emitted from the blood and this organ or region. During the scan, tracings of the emitted radiation are detected by the system creating an image of the distribution of the radiopharmaceutical in the patient. The image can show the circulatory system and/or the relative absorption of the radiopharmaceutical in various regions or organs. Integration of the anatomical data from the CT scan with the metabolic data from the PET scan in the PET-CT image gives physicians visual information to determine if disease is present, the location and extent of disease, and track how rapidly it is spreading. The PET-CT system is particularly helpful in difficult-to-treat regions (e.g. head and neck area, mediastinum, postsurgical abdomen) and localization of the treatment area for the patients receiving radiation therapy or chemotherapy.

Typically, in the process of the reconstruction a PET-CT image, the PET image representation is converted from the PET image space into the CT image space to create a composite image for clinical interpretation. Prior to the scan, the PET and CT systems are aligned mechanically; however, in most cases, there is a minor correction that needs to be applied for a precise alignment of the PET image and the CT image before fusing. Currently, the transformation parameters are derived during calibration, such as using a phantom which is imageable in both modalities.

In the past, PET and CT image data were both reconstructed into 3D rectangular arrays of voxels, but of different scale (voxels of different sizes). Transforming between the cartesian grids of the lower resolution PET image and the higher resolution CT image was relatively straightforward, but sometimes added transformation or interpolation errors and degraded accuracy and image quality.

Now the PET image is often reconstructed into a blob space with a non-cartesian grid. Unlike voxels, which are of uniform value throughout, the values within each blob are non-uniform. Moreover, the blobs overlap. Currently, the reconstructed PET blob image is first transformed into conventional voxel-based, cartesian grid image. Because the PET voxels are again a different size from the CT voxels, the PET voxel image is then transformed into the CT voxel size. Performing two interpolations compounds the inherent transform related errors.

The present invention provides a new and improved imaging apparatus and method which overcomes the above-referenced problems and others.

In accordance with one aspect of the present invention, a diagnostic imaging system is disclosed. A first scanner obtains a first set of electronic data of a region of interest of a subject. A second scanner obtains a second set of electronic data of the region of interest of the subject. A first reconstruction means reconstructs the first set into a non-voxel space first scanner image representation in a non-voxel image space. A second reconstruction means reconstructs the second set into a second image representation in a second image space. A means directly converts the non-voxel space first scanner image representation of the first set into the second image space.

In accordance with another aspect of the present invention, a method of diagnostic imaging is disclosed. A first set of electronic data of a region of interest of a subject is obtained. A second set of electronic data of the region of interest of the subject is obtained. The first set is reconstructed into a non-voxel space first scanner image representation in a non-voxel image space. The second set is reconstructed into a second image representation in a second image space. The non-voxel space first scanner image representation of the first set is directly converted into the second image space.

One advantage of the present invention resides in improving the overall image quality.

Another advantage resides in decreasing the computational and memory demands.

Another advantage resides in more accurate fused images.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 2:
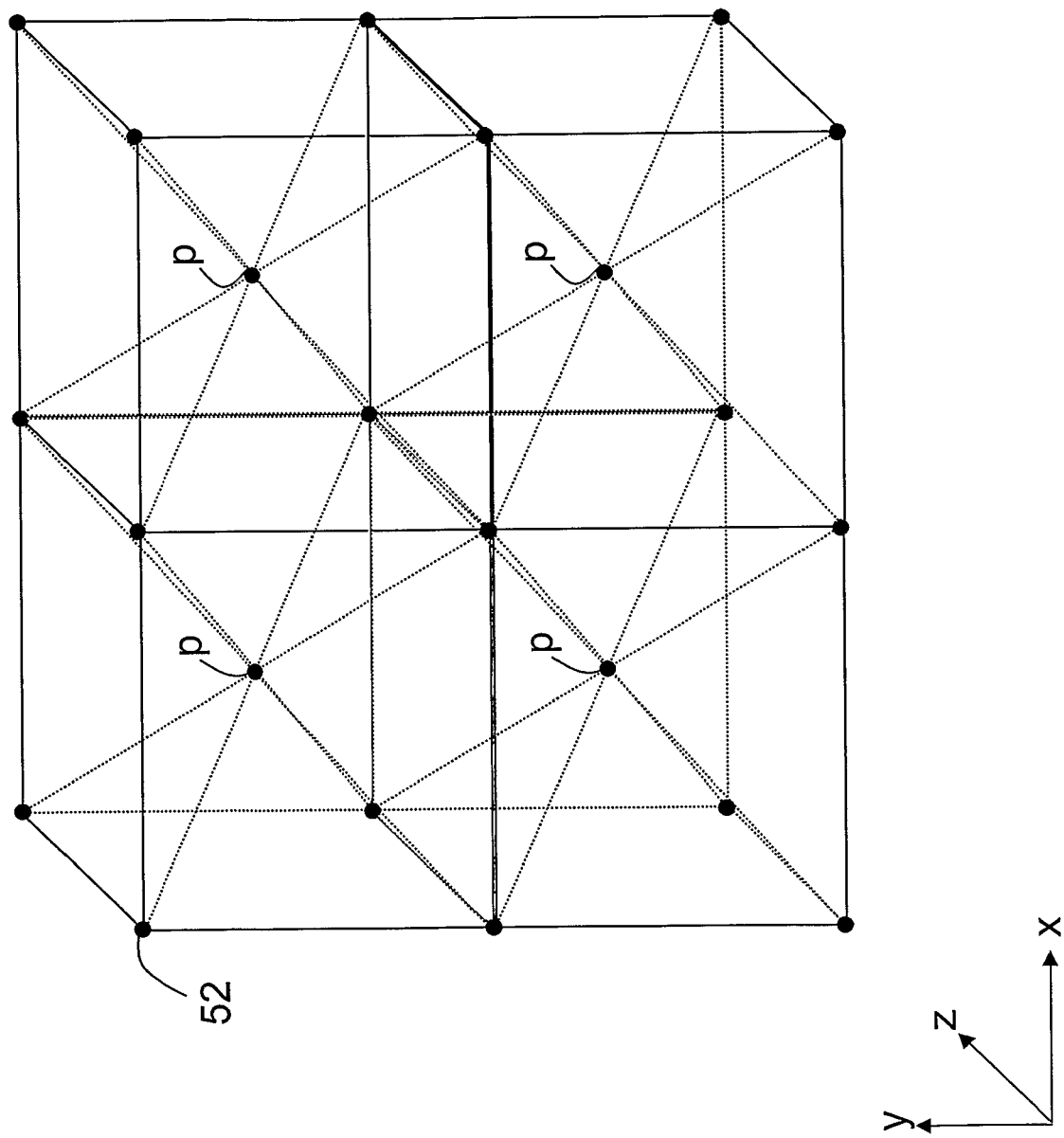
Figure 3:
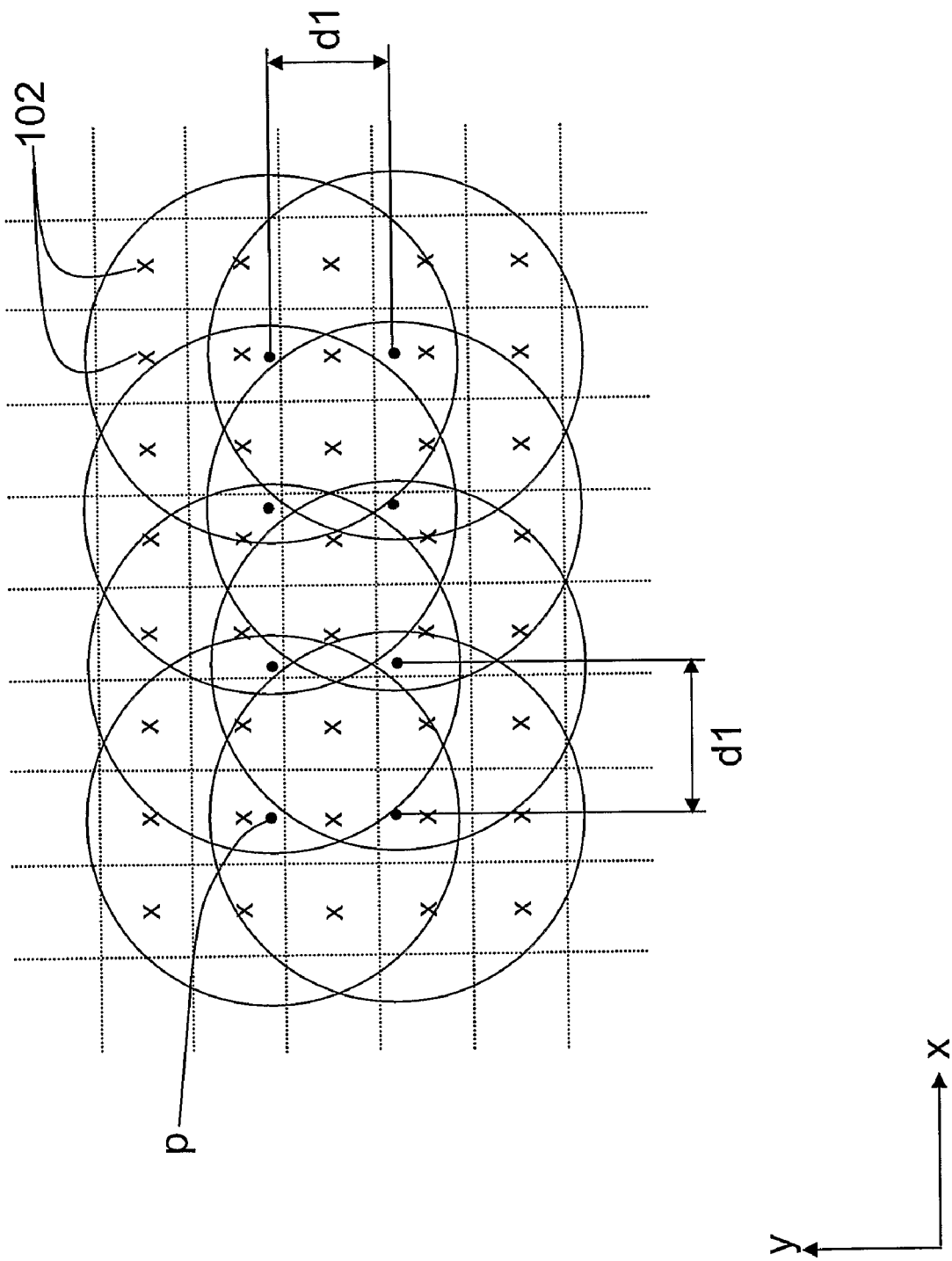
Figure 4:
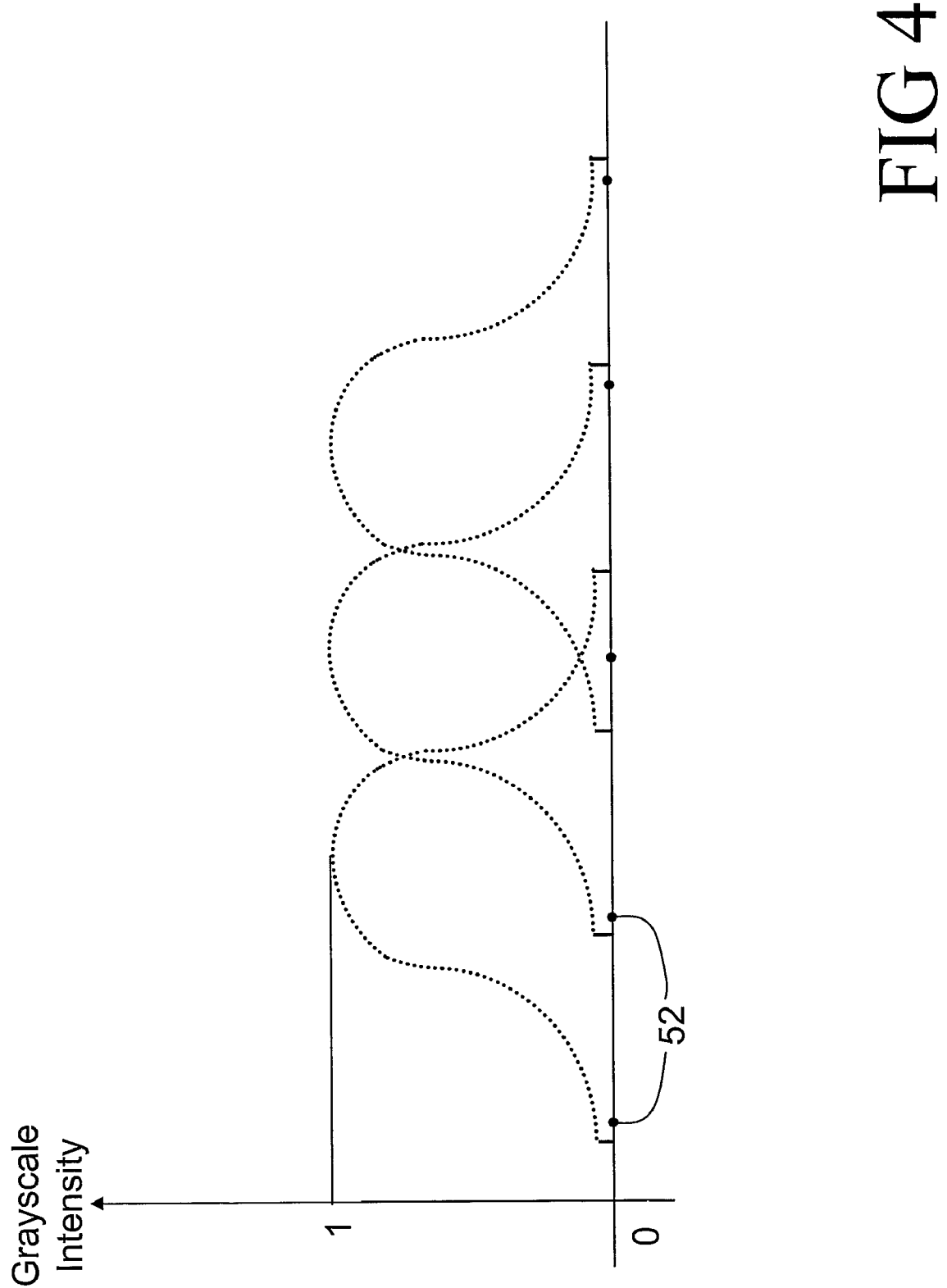
Figure 5:
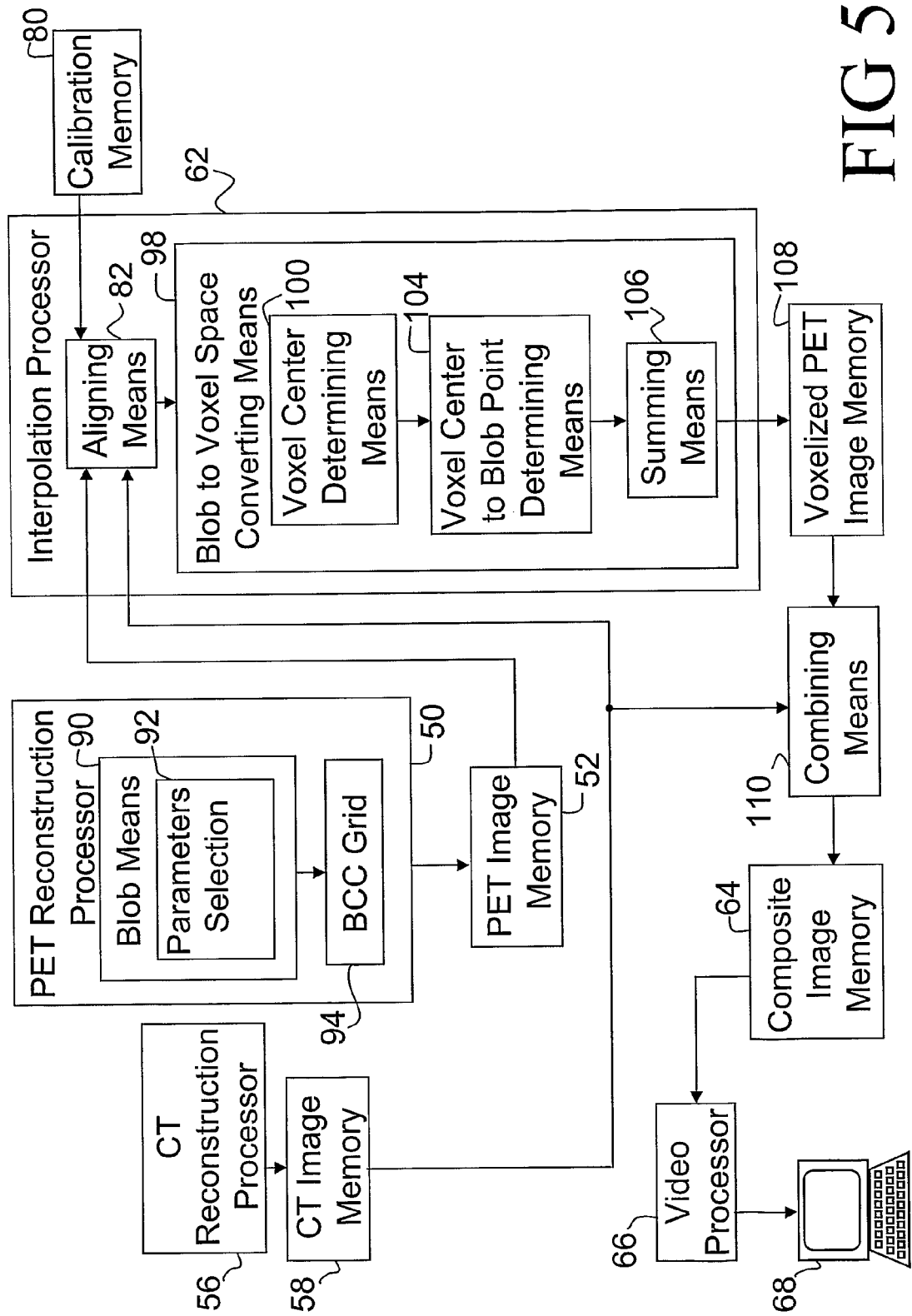

FIG. 1 is a diagrammatic illustration of a multi-modality diagnostic imaging system;

FIG. 2 diagrammatically shows a body centered cubic grid;

FIG. 3 diagrammatically shows 2D blobs projected into cartesian grid image space;

FIG. 4 is a diagrammatic representation of grayscale intensity values within a blob by a smooth curve function; and FIG. 5 is a diagrammatic illustration of a portion of a multi-modality diagnostic imaging system.

With reference to FIG. 1, a multi-modality system 10 includes a nuclear imaging system 12 and a computed tomography (CT) scanner 14. The CT scanner 14 includes a non-rotating gantry 16. An x-ray tube 18 is mounted to a rotating gantry 20. A bore 22 defines an examination region 24 of the CT scanner 14. An array of radiation detectors 26 is disposed on the rotating gantry 20 to receive radiation from the x-ray tube 18 after the x-rays transverse the examination region 24. Alternatively, the array of detectors 26 may be positioned on the non-rotating gantry 16.

The nuclear imaging system 12 preferably includes a positron emission tomography (PET) scanner 28 which is mounted on tracks 30. Of course, SPECT and other nuclear imaging systems are also contemplated. The tracks 30 extend in parallel to a longitudinal axis of a subject support or couch 32, thus enabling the CT scanner 14 and PET scanner 28 to form a closed system. A moving means 34, such as a motor and a drive, is provided to move the scanner 28 in and out of the closed position. Detectors 36 are arranged around a bore 38 which defines an examination region 40. In the PET system, the detectors 36 are preferably arranged in a stationary ring, although rotatable heads are also contemplated. In the SPECT system, the detectors 36 are preferably incorporated into individual heads, which are mounted for rotational and radial movement relative to the patient. A couch moving means 42, such as a motor and a drive, provides a longitudinal movement and vertical adjustment of the couch 32 in the examination regions 24, 40.

As will be discussed in a greater detail below, the PET scanner 28 acquires electronic data which is reconstructed into a PET blob image by a PET reconstruction processor or process 50 and stored in a PET blob image memory 52. A suitable blob reconstruction algorithm is described in Lewitt (1990) and Lewitt (1992).

With reference to FIGS. 2 and 3, blobs can be conceptualized as spheres each centered on a corner point or a body center point of a body-centered cubic arrangement. The spheres are larger than the spacing of corner points 52, e.g., a diameter equal to 2½ times the corner to corner point spacing. Within each blob, the gray scale (or intensity value) is largest at the center and decreases toward the periphery with a spherically symmetric Bessel function, Gaussian, or other smooth or piecewise smooth curve as seen in FIG. 4.

With reference again to FIG. 1, the CT scanner 14 acquires the scan data which is reconstructed into a 3D CT voxel image by a CT reconstruction processor or process 56 and stored in a CT image memory 58. The CT data is preferably reconstructed into rectangular voxels defined by a 3D cartesian coordinate system. Typically, the CT voxels are significantly smaller than the PET corner point spacing, e.g. 1 to 3 mm versus 3 to 6 mm. An interpolation processor or process 62 interpolates the PET blob image directly into the CT voxel space, i.e. an image with the same 3D cartesian grid and voxel size as the CT image. Once the PET and CT images are in the same space, they are readily summed or otherwise combined. A resultant composite image is stored in a composite image memory 64. A video processor 66 processes the received composite PET-CT data for a display on one or more monitors 68.

With continuing reference to FIG. 1, sometime prior to scanning, a transformation matrix between the CT and PET portions of the imaging system 10 is determined by using a phantom 70 which includes CT-nuclear markers 72. An exemplary CT-nuclear marker 72 includes a disc or sphere of dense, CT imageable material and radioisotope marker at its center. The marker might be constructed of glass-filled Teflon or other suitable material, having a significantly different CT number from the phantom, to be readily identified during the CT scan. Typically, the radioisotope marker is the vial containing an isotope with a relatively long half-life, preferably of more than 100 days, to prevent frequent replacements. For the PET-CT combination, a preferential isotope is Na-22 with a half-life of 2.6 years. However, isotopes with shorter half-lives such as Ge-68 might be used as well. For the SPECT-CT combination, the isotope for the radioisotope marker is selected from the isotopes having a half-life more than 100 days and a strong energy peak between 50 keV and 600 keV. Examples of appropriate SPECT imageable isotopes are Co-57, Gd-153, Cd-109, Ce-139, Am-241, Cs-137 and Ba-133.

The couch 32 with the phantom 70 is moved by the couch moving means 42 into the examination region 40 for a 3D image to be generated by the PET scanner 28. Electronic data is reconstructed into a PET image by the PET reconstruction processor or process 50. The coordinates of a center of mass of each radioisotope marker are determined.

Next, the couch moving means 42 moves the couch 32 to position the phantom 70 in the CT scanner examination region 24, where the CT image is taken. Electronic data is reconstructed into a 3D CT image of the center of mass of the CT markers by the CT reconstruction processor 56. The radioisotope markers position coordinates, calculated for the PET image, are translated into CT image space using the known geometry and mechanical alignment of the PET and CT scanners. The coordinates of the corresponding markers are determined. The transformation parameters or matrix is next determined, e.g. the amount of linear shift, scaling, rotation, and, optionally, non-linear translations to bring the PET image and the CT image into precise alignment. The transformation parameters are stored in a calibration memory 80 and are used by an aligning processor or means 82 to align PET and CT images with each other in the interpolation process 62 of subsequent scans. For example, the aligning means 82 can apply the determined transform to the corner and center points of the PET blob image to align the blob image with the CT image.

With continuing reference to FIG. 1 and further reference to FIG. 5, the couch 32 with an object is moved by the couch moving means 42 into the examination region 40 for a 3D image to be generated by the PET scanner 28. Electronic data is reconstructed into a blob space by the PET reconstruction processor 50.

Generally, the continuous distribution $f(x, y, z)$ of a 3D scanned object can be approximated by a sum of scaled and shifted overlapping copies of the basis function $\Phi(x)$ whose centers are arranged on a grid with grid points $p(x_n, y_n, z_n)$:

$$f(x, y, z) = \sum_{n=0}^{N-1} c_n \Phi(x - x_n, y - y_n, z - z_n) \qquad (1)$$

where $\{(x_n, y_n, z_n), n=0{\sim}N-1\}$ is a set of N sampling points uniformly distributed in the 3D space with sampling interval $\Delta$, $c_n$ is the image coefficient at each sampling point n.

Incorporation of spherically-symmetric volume elements or blobs into iterative reconstruction algorithms is well known in the reconstruction field. Generally, blobs are characterized by a spherical symmetry, a smooth, bell-shaped profile which tapers smoothly in the radial direction from one at the center of the sphere to zero at the surface of the sphere, and limited support. A spherical-symmetric basis function or blob has the form:

$$\Phi^{blob}(x,y,z) = b(r) = b(\sqrt{x^2+y^2+z^2}) \qquad (3)$$

where r is the radial distance from the origin.

Preferably, a blob or process means 90 reconstructs the electronic data into the spheres using a Kaiser-Bessel window function having the following form inside the sphere of a radius a:

$$b_{m,a,\alpha}(r) = \begin{cases} \dfrac{1}{I_m(\alpha)}\left[\sqrt{1-(r/a)^2}\right]^m I_m[\alpha\sqrt{1-(r/a)^2}] & \text{for } 0 \le r \le a \\ 0 & \text{otherwise} \end{cases} \qquad (4)$$

where r is the radial distance from the blob center, $I_m$ denotes the modified Bessel function of the first kind of order m, a is the radius of the support of the blob (relative to the sampling interval Δ), α is a non-negative real number controlling the shape of the blob, e.g. the function roll-off in the radial direction, and m is a non-negative integer controlling the smoothness of the blob at its boundary r=a.

A parameters selection means 92 selects the three parameters m, a, and α which influence the result yielded by the interpolation process 62. Small values of α result in wide blobs, while large values of α result in blobs having narrow peak and long tails. The parameter m allows to control the continuity of the blob at the function's radial limit (r=a). For example, if m is equal to 0, the blob is not continuous at the boundary; and if m is greater than 0, the blob is a continuous function with (m−1) continuous derivatives at the boundary. Compared with the conventional reconstruction which uses voxel basis function in the image reconstruction, the blob-based reconstruction has better contrast noise tradeoffs.

A grid means 94 shifts the centers of the PET blobs to the centers of cubes. Preferably, the grid is a body-center cubic (BCC) grid as illustrated in FIG. 2, instead the conventional voxel cubic grid. The simple cubic grid is well suited for voxel based reconstruction; however, it has been shown to be not the optimum grid for the blob-based reconstruction as it leads to large computational demands. The body-center cubic grid enables a more isotropic distribution of the blob in the 3D space and requires $\sqrt{2}$ times fewer grid points than the simple cubic grid for the same image representation accuracy. Using the body-center cubic grid, the grid means 94 spaces the blob centers p(x, y, z) a distance d1 equal to bccRsz (relative to the sampling interval Δ) from each other in the transverse (x, y) plane. In the axial z direction, the grid means 94 spaces the blob centers p(x, y, z) a distance d2 equal to bccRsz/2 from each other. The odd transverse plane blob centers p'(x, y, z) are shifted bccRsz/2 from the even transverse plane blob centers p"(x, y, z). Therefore, for any blob n with integer index (i, j, k), the blob center p(x, y, z) is located at $$x_n^{blob} = \begin{cases} (i - N_x^{blob}/2 + 0.5) * bccRsz & \text{if } k \text{ is even} \\ (i - N_x^{blob}/2 + 1.0) * bccRsz & \text{if } k \text{ is odd} \end{cases} \quad (5)$$

$$y_n^{blob} = \begin{cases} (j - N_y^{blob}/2 + 0.5) * bccRsz & \text{if } k \text{ is even} \\ (j - N_y^{blob}/2 + 0.5) * bccRsz & \text{if } k \text{ is even} \end{cases}$$

$$z_n^{blob} = (k - N_z^{blob}/2 + 0.5) * bccRsz/2.0,$$

relative to sampling interval Δ where $N_x^{blob}$, $N_y^{blob}$ and $N_z^{blob}$ are the matrix size of the object in the blob space.

The reconstructed PET image in the blob format is stored in the PET image memory 52.

With continuing reference to FIGS. 1 and 5, the couch moving means 42 moves the couch 32 to position the object in the CT scanner examination region 24, where the CT image is taken. Preferably, the object is moved to the position in the CT examination 24 region that is geometrically and mechanically predicted as being the same as its imaged position in the PET imaging region. Electronic data is reconstructed into a 3D CT image by the CT reconstruction processor 56 and stored in the CT image memory 62.

The interpolation processor or process 62 interpolates the PET blob data into the CT voxel space. More specifically, the aligning means 82 applies the previously determined transformation matrix, e.g. rotation and translation to align the blob space with the CT voxel space. In one embodiment, the aligning means 82 applies an affine transform to the blob grid points p(x, y, z) to align the blob space to the voxel space. Alternately, the aligning means 82 can apply the previously determined transformation to the bcc grid in the grid means 94 such that the image in the PET image memory is aligned with the image in the CT image memory. A PET image space to CT image space converting means 98 converts the PET blob image to the CT voxel image:

$$f(x, y, z) = \sum_{n=0}^{N-1} c_n \Phi_{\Delta^{PET}}^{blob}(x - x_n, y - y_n, z - z_n) \quad (6)$$

$$= \sum_{m=0}^{M-1} t_m \Phi_{\Delta^{CT}}^{voxel}(x - x_m, y - y_m, z - z_m)$$

where $f(x, y, z)$ is a composite 3D image representation, $\Phi^{blob}$ is the PET blob image representation, $\Phi^{voxel}$ is the CT image voxel representation, n is a number of sampling points in the PET image space, m is a number of sampling points in the CT image space, $\Delta^{PET}$ is PET image voxel size (sampling interval), $\Delta^{CT}$ is the CT voxel size, $c_n$ is the image coefficient at each sampling point n, $t_m$ is the image coefficient at each sampling point m which depend on the number of blobs overlying a center of the CT voxel v.

More specifically, a voxel center determining means 100 determines a position of a center point 102 of each CT voxel v. A voxel center to blob point converting means 104 projects the voxel v into the blob space and determines a point v' which corresponds to a center of the voxel in the PET blob domain. The value of each point in the blob space is the sum of density values at that point of all blobs that cover that given point. A summing means 106 sums up all overlapping blobs that overlie the point v'. More specifically, the summing means 106 determines the PET image coefficient $t_m$ for the center m=(i', j', k') of each CT voxel v:

$$t_m = \sum_{n=0}^{N-1} c_n \Phi_{\Delta^{PET}}^{blob}(x_m - x_n, y_m - y_n, z_m - z_n) \quad (7)$$

$$x_m = x^{offset}/\Delta^{PET} + (i' - M_x^{voxel}/2 + 0.5) * \Delta^{CT}/\Delta^{PET} \quad (8)$$

$$y_m = y^{offset}/\Delta^{PET} + (j' - M_y^{voxel}/2 + 0.5) * \Delta^{CT}/\Delta^{PET}$$

$$z_m = z^{offset}/\Delta^{PET} + (k' - M_z^{voxel}/2 + 0.5) * \Delta^{CT}/\Delta^{PET}$$

where $M_x^{voxel}$, $M_y^{voxel}$ and $M_z^{voxel}$ are the matrix size of the object in the CT voxel space, and ($x^{offset}$, $y^{offset}$, $z^{offset}$) is the offset of the CT image origin relative to the PET image origin.

In one embodiment, the summing means 106 sums up the points that correspond to the entire area of the voxel v, not only the center point of the voxel v. Of course, the blob densities corresponding to some parts of the CT voxel v may be weighted more heavily than others. The CT space PET image is stored in a voxelized PET image memory 108. A combining means 110 combines the like-formatted PET and CT images and loads the combined image into the composite image memory 64. Various combinations are contemplated. In one example, the two images are simply summed. In another, the PET image is displayed in color and the CT in black and white. In another, the CT image is static and the PET image is displayed as a temporally evolving series of images that show the uptake or washout of the radiopharmaceutical. Numerous other composite images are also contemplated.

By converting the PET blob image to the CT voxel image space directly skipping an intermediate voxelization of the PET image into PET voxel image space, the resultant image has a more continuous profile, better quality and demands less computational effort.

Of course, it is also contemplated that the interpolation process 62 can convert the data from the 2D PET blob space to the 2D CT pixel space and vice versa.

The examples of the spatially localized functions that are suitable for converting the PET electronic data into the blobs for a use in 3D/2D image interpolation process 62 include rectangular shaped basis functions, such as pixel for 2D and voxel for 3D, bilinear functions in 2D, Cubic B-spline function in 2D, truncated Gaussian in 2D and 3D, product of two raised-cosine bell in 2D, spherically symmetric basis functions such as spherical symmetric generalized Kaiser-Bessel basis function, prolate spheroidal wave functions, and the like, orthogonal-oriented quadrature pyramid (HOP) basis function, and others. The examples of the spatially non-localized functions that are suitable for converting the PET electronic data into the blobs for a use in 3D/2D image interpolation process 62 include spatially non-localized basis function, Gaussian basis function, sine/cosine wave basis function such as Fourier transform, Fourier transform of the generalized Kaiser-Bessel basis function, wavelet basis function, and others. Another example of the basis function that is suitable for converting the PET electronic data into the blobs for a use in 3D/2D image interpolation process 62 is the natural pixel basis function.

The invention has been described with reference to the preferred embodiments. Modifications and alterations may occur to others upon a reading and understanding of the preceding detailed description. It is intended that the invention be constructed as including all such modifications and alterations insofar as they come within the scope of the appended claims or the equivalents thereof.

The invention claimed is:
1. A diagnostic imaging system comprising:
a first scanner for obtaining a first set of electronic data of a region of interest of a subject;
a second scanner for obtaining a second set of electronic data of the region of interest of the subject; and
one or more processors programmed to:
reconstruct the first set of electronic data into a non-voxel space first scanner image representation in a non-voxel image space;
reconstruct the second set of electronic data into a second image representation in a second image space;
convert the non-voxel image space first scanner image representation of the first set of electronic data into the second image space; and
wherein the one or more processors reconstruct the first electronic data set into blobs.
2. The diagnostic imaging system as set forth in claim 1, wherein the blobs are arranged in a body-centered cubic grid and the second image space is a Cartesian, voxel image space.
3. The diagnostic imaging system as set forth in claim 2, the blobs are sized to overlap each other.
4. The diagnostic imaging system as set forth in claim 1, wherein the second image space is a voxel image space and the one or more processors are further programmed to:
determine a center point of each voxel v of the voxel image space; and
determine a point in the non-voxel image space image representation which corresponds to each determined voxel center to define a voxel image space first scanner image.
5. The diagnostic imaging system as set forth in claim 4, wherein the non-voxel image space includes blobs arranged on a non-Cartesian grid, which blobs partially overlap and one or more processors are further programmed to:
sum all blobs which overlap each determined point in the non-voxel image space image representation to reconstruct a composite voxel image $f(x, y, z)$:

$$f(x, y, z) = \sum_{n=0}^{N-1} c_n \Phi_{\Delta^2}^{blob}(x - x_n, y - y_n, z - z_n)$$
$$= \sum_{m=0}^{M-1} t_m \Phi_{\Delta^1}^{voxel}(x - x_m, y - y_m, z - z_m)$$

where $f(x, y, z)$ is a composite 3D image representation, $\Phi^{blob}$ is the non-voxel image space image representation, $\Phi^{voxel}$ is the voxel space first scanner image representation, n is a number of sampling points in the non-voxel image space image, m is a number of sampling points in the voxel image, $\Delta^2$ is a blob size or a sampling interval, $\Delta^1$ is a voxel size or a sampling interval in the voxel image space, $c_n$ is the image coefficient at each sampling point n, $t_m$ is the image coefficient at each sampling point m which depend on a number of blobs overlying the center of the voxel of the voxel image space.
6. The diagnostic imaging system as set forth in claim 4, wherein the one or more processors are further programmed to:
apply a previously determined system transformation matrix to one of: (a) the voxel space first scanner image representation prior to determining the points in the non-voxel image space image representation which points correspond to the voxel image space voxel centers, (b) the voxel image space, and (c) the non voxel image space first scanner image representation to register the non-voxel image space image representation and the voxel space image representations with one another.
7. The diagnostic imaging system as set forth in claim 6, wherein the one or more processors are further programmed to:
combine the voxel image space first scanner image representation with the second scanner image representation.
8. The diagnostic imaging system as set forth in claim 1, wherein the first and second scanners include at least two of: PET, SPECT, MRI, ultrasound, fluoroscopy, CT, and digital x-ray.
9. A diagnostic imaging system comprising:
a first scanner for obtaining a first set of electronic data of a region of interest of a subject;
a second scanner for obtaining a second set of electronic data of the region of interest of the subject; and
one or more processors programmed to:
reconstruct the first set of electronic data into a non-voxel space first scanner image representation in a non-voxel image space;
reconstruct the second set of electronic data into a second image representation in a second image space;
convert the non-voxel image space first scanner image representation of the first set of electronic data into the second image space wherein the non-voxel image space is a non-Cartesian image space and the second image space is a Cartesian voxel image space.

10. A diagnostic imaging system comprising:
a first scanner for obtaining a first set of electronic data of a region of interest of a subject;
a second scanner for obtaining a second set of electronic data of the region of interest of the subject;
a first reconstruction processor which reconstructs the first set into a non-voxel space first scanner image presentation in a non-voxel image space, the non-voxel image space including a plurality of blobs, each blob being centered on a body center point of a body-centered cubic grid;
a second reconstruction processor which reconstructs the second set into a second image representation in a second image space, the second image space being a voxel-based cartesian grid image; and
a processor which directly converts the non-voxel space first scanner image representation into the second image space.

11. The diagnostic imaging system as set forth in claim 10, wherein the blob is described by a Kaiser-Besel function b(r):

$$b_{m,a,\alpha}(r) = \begin{cases} \frac{1}{I_m(\alpha)} \left[\sqrt{1-(r/a)^2}\right]^m I_m\left[\alpha\sqrt{1-(r/a)^2}\right] & \text{for } 0 \le r \le a \\ 0 & \text{otherwise} \end{cases}$$

where r is the radial distance from the blob center, $I_m$ denotes the modified Bessel function of the first kind of order m, a is the radius of the support of the blob, $\alpha$ is a non-negative real number controlling the shape of the blob, and m is a non-negative integer controlling the smoothness of the blob at its boundary r=a.

12. The diagnostic imaging system as set forth in claim 11, wherein the one or more processors further select optimal parameters m, a and $\alpha$ to control a shape of the blob.

13. A method of diagnostic imaging comprising:
receiving a first set of electronic data of a region of interest of a subject from a first scanner;
receiving a second set of electronic data of the region of interest of the subject from a second scanner;
reconstructing the first set of electronic data into a non-voxel space first scanner image representation in a non-voxel image space;
reconstructing the second set of electronic data into a second image representation in a voxel-based Cartesian image space;
determining a center point of each voxel in the voxel-based cartesian image space;
determining a point in the non-voxel space first scanner image representation which corresponds to each determined voxel center point;
determining a data value corresponding to each determined center point in the non-voxel space image representation to generate a voxel space first scanner image representation; and
displaying on a display device at least one of:
the voxel-based Cartesian image space second image representation,
the voxel space first scanner image representation, and
a combination of the voxel-based Cartesian image space image representation and the voxel space first scanner image representation.

14. The method as set forth in claim 13, wherein reconstructing the first set of electronic data includes reconstructing the first set of electronic data into blobs arranged on a body centered cubic grid and overlapping at least an adjacent blob and further including:
summing all blobs which overlap each determined point in the blob image representation which point corresponds to the voxel center; and
reconstructing a composite voxel image $f(x, y, z)$:

$$f(x, y, z) = \sum_{n=0}^{N-1} c_n \Phi_{\Delta^2}^{blob}(x-x_n, y-y_n, z-z_n)$$
$$= \sum_{m=0}^{M-1} t_m \Phi_{\Delta^1}^{voxel}(x-x_m, y-y_m, z-z_m)$$

where $f(x, y, z)$ is a composite 3D image representation, $\Phi^{blob}$ is the blob image representation, $\Phi^{voxel}$ is the voxel space first scanner image representation, n is a number of sampling points in the blob image, m is a number of sampling points in the voxel image, $\Delta^2$ is a blob size or a sampling interval, $\Delta^1$ is a voxel size or a sampling interval in the voxel image space, $c_n$ is the image coefficient at each sampling point n, $t_m$ is the image coefficient at each sampling point m which depend on a number of blobs overlying the center of the voxel.

15. The method as set forth in claim 13, further including:
combining the voxel space first scanner image representation with the second scanner image representation.

16. The method as set forth in claim 13, wherein the first and second scanners include at least two of: PET, SPECT, MRI, ultrasound, fluoroscopy, CT, and digital x-ray.

17. A diagnostic imaging system for performing the method of claim 13.

18. A multi-modality imaging system comprising:
first scanner,
second scanner,
data processor programmed to perform the method of claim 13.

19. An imaging method comprising:
obtaining functional image data from a region of a subject and reconstructing the functional data into a functional image in a non-voxel image space;
obtaining anatomical image data of the region of the subject and reconstructing the anatomical image data in an anatomical image in a voxel image space;
converting the functional image directly from the non-voxel image space directly to the voxel image space of the anatomical image; and
displaying at least one of the functional image, the anatomical image, and a combination of the functional and anatomical images.

20. The imaging method as set forth in claim 19, wherein the functional image is a blob image and the non-voxel image space is a non-Cartesian image space.

21. The imaging method as set forth in claim 19, further comprising combining the functional and anatomical images in the voxel image space.

22. The imaging method as set forth in claim 19, wherein the converting step includes:
determining a center point of voxels of the anatomical image;
determining points in the functional image which correspond to the center points of the functional image.

23. The method as set forth in claim 22, wherein reconstructing the first set of electronic data includes reconstructing the first set of electronic data into blobs, each blob being defined by a Kaiser-Bessel function b(r):

$$b_{m,a,\alpha}(r) = \begin{cases} \frac{1}{I_m(\alpha)}\left[\sqrt{1-(r/a)^2}\right]^m I_m\left[\alpha\sqrt{1-(r/a)^2}\right] & \text{for } 0 \leq r \leq a \\ 0 & \text{otherwise} \end{cases}$$

where r is the radial distance from the blob center, $I_m$ denotes the modified Bessel function of the first kind of order m, a is the radius of the support of the blob, $\alpha$ is a non-negative real number controlling the shape of the blob, and m is a non-negative integer controlling the smoothness of the blob at its boundary r=a.

24. The method as set forth in claim 23, further including:
selecting optimal parameters m, a and $\alpha$ to control a shape of the blob.

* * * * *